United States Patent
Sawada et al.

(10) Patent No.: US 8,352,003 B2
(45) Date of Patent: Jan. 8, 2013

(54) SENSOR UNIT AND BIOSENSOR

(75) Inventors: Renshi Sawada, Fukuoka (JP); Eiji Higurashi, Tokyo (JP)

(73) Assignees: Kyushu University, National University Corporation, Fukuoka (JP); The University of Tokyo, Tokyo (JP)

( * ) Notice: Subject to any disclaimer, the term of this patent is extended or adjusted under 35 U.S.C. 154(b) by 1614 days.

(21) Appl. No.: 11/667,108

(22) PCT Filed: Nov. 1, 2005

(86) PCT No.: PCT/JP2005/020122
§ 371 (c)(1),
(2), (4) Date: May 7, 2007

(87) PCT Pub. No.: WO2006/051726
PCT Pub. Date: May 18, 2006

(65) Prior Publication Data
US 2008/0097172 A1    Apr. 24, 2008

(30) Foreign Application Priority Data
Nov. 9, 2004  (JP) ................................ 2004-324937

(51) Int. Cl.
*A61B 5/1455* (2006.01)

(52) U.S. Cl. ...................................... 600/310; 600/324

(58) Field of Classification Search .................. 600/310, 600/316, 322–324, 326, 338, 340, 473, 476; 356/41
See application file for complete search history.

(56) References Cited

U.S. PATENT DOCUMENTS

| 5,490,506 A | 2/1996 | Takatani et al. |
| 5,893,364 A * | 4/1999 | Haar et al. ..................... 600/310 |
| 7,315,752 B2 * | 1/2008 | Kraemer et al. .............. 600/310 |

FOREIGN PATENT DOCUMENTS

| EP | 0 771 546 | 5/1997 |
| JP | 62-60051 | 4/1987 |
| JP | 2002-45342 | 2/2002 |
| JP | 2002-330936 | 11/2002 |
| JP | 2004-229920 | 8/2004 |

* cited by examiner

*Primary Examiner* — Eric Winakur
*Assistant Examiner* — Chu Chuan (JJ) Liu
(74) *Attorney, Agent, or Firm* — Wenderoth, Lind & Ponack, L.L.P.

(57) ABSTRACT

A highly miniaturized biosensor and a sensor unit, which can meet a demand for further miniaturization. With this invention, miniaturization is possible, and the number of production steps including those for assembling individual parts can be reduced. Accordingly, mass production will be possible, and cost reduction and high reliability will be achieved. A light emitting unit (21) and a light receiving unit (22) are disposed in a same recess (24) formed on a surface of a semiconductor substrate (23), and a light shielding cover substrate (27) having a first light guide section (25) and a second light guide section (26) is disposed on an upper side of the semiconductor substrate (23). Since the light receiving unit (22) is formed with arrayed light receiving elements (28), the same number of the second light guide sections (26) as the light receiving elements (28) are provided on the light shielding cover substrate (27), and the light receiving surfaces of the light receiving elements (28) are connected to one end of each of the second light guiding sections (26) so as to conform to each other without any gap.

4 Claims, 15 Drawing Sheets

Experiment A

Experiment B

Experiment C

Experiment D

Experiment E

Experiment F

Experiment G

Experiment H

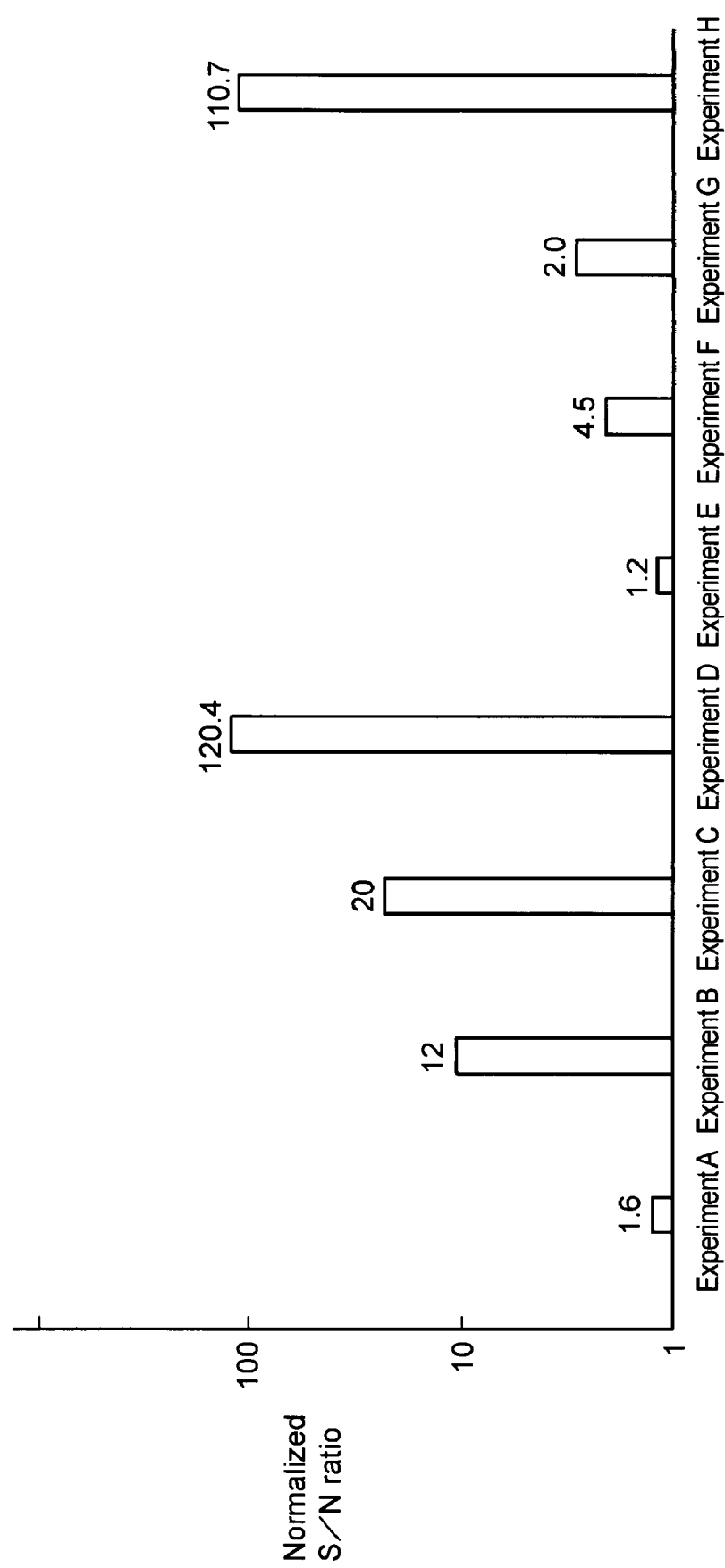

SENSOR UNIT AND BIOSENSOR

FIELD OF THE INVENTION

The present invention relates to a biosensor that utilizes scattered light or the like from living tissue to collect information regarding liquid matter inside a living body such as a blood flow inside living tissue under observation, and to a sensor unit used in this biosensor.

BACKGROUND ART

Patent Document 1 is a conventional technology document that describes a structure of a sensor chip used in a conventional blood flowmeter. FIG. 13 illustrates a sensor chip of a conventional blood flowmeter described in Patent Document 1. In the conventional sensor chip illustrated in FIG. 13 includes a semiconductor laser 1 as a light emitting device, a photodiode 2 as a light-receiving element, and an optical waveguide 3 for guiding light emitted from the light emitting device in the form of divergent light, focused light, or parallel light and irradiating it toward living tissue situated outside, all of which are integrated on a single semiconductor substrate.

It further includes a shielding block 4 attached to the substrate so as to individually enclose the semiconductor laser 1 and the photodiode 2 in order to prevent light from the semiconductor laser 1 from directly entering the photodiode 2. The photodiode 2 is an edge-illuminated refracting-facet photodiode, in front of which a second light shielding board having a certain gap may be provided.

A blood flowmeter such as the above-described type measures a blood flow rate, a blood volume, a blood flow velocity, and a pulse rate by detecting interference (by heterodyne detection) between scattered light from living tissue at rest and scattered light from red corpuscles (scattering particles) moving through a capillary of living tissue (scattered light experiencing the Doppler shift $\Delta f$ in accordance with the blood flow velocity). This measurement principle is described, for example, in a document by M. D. Stern: In vivo evaluation of microcirculation by coherent light scattering, Nature, vol. 254, pp. 56-58 (1975).

In order to achieve miniaturization and facilitate the assembly of individual parts, the inventors of the present invention invented a blood flowmeter equipped with a sensor unit having a structure where a light emitting device and a light-receiving element are disposed in a recess formed on a surface of a single semiconductor substrate, a cover substrate with a light shielding film for shielding undesired scattered light is disposed on an upper surface of the semiconductor substrate, light emitted from the light emitting device is irradiated toward living tissue situated outside through the cover substrate, and scattered light from the living tissue is received by the light receiving element through the cover substrate. The details are described in Patent Document 2.

Furthermore, Patent Document 3 describes a tissue blood flowmeter whose objective is to prevent a disturbance in phase of the Doppler shift due to the bombardment with the cladding of optical fiber of reflected laser light from the sample. In this tissue blood flowmeter, a pinhole is provided coaxially with the optical fiber between the optical fiber and a photoelectric conversion device, and laser light guided by the optical fiber is directed to the photoelectric conversion device through the pinhole.

Patent Document 1: Unexamined Japanese Patent Publication No. 2002-330936.
Patent Document 2: Unexamined Japanese Patent Publication No. 2004-229920.
Patent Document 3: Unexamined Japanese Patent Publication No. 2002-45342.

SUMMARY OF THE INVENTION

Problems to be Solved by the Invention

According to the invention described in Patent Document 2, a cover substrate with a light shielding film for shielding undesired scattered light is disposed on an upper surface of a semiconductor substrate, thereby realizing a structure that functions both as a conventional light shielding board and a protective cover glass in a fewer number of production steps. This reduces production cost and can greatly contribute to the miniaturization of the device and the simplification of production steps. However, a demand for further miniaturization of blood flowmeters are growing, and further miniaturization results in an arrangement where the light emitting unit and the light receiving unit are disposed in the same recess. Accordingly, problems arise as part of light emitted from the light emitting unit directly enters the light receiving unit without passing through the living tissue, thereby reducing the relative intensity of light signals and deteriorating the S/N ratio. Furthermore, if arrayed photodiodes are used as the light receiving unit in order to measure a two-dimensional distribution of blood, then, because of a gap present between the photodiodes and the light shielding film for shielding undesired scattered light, the scattered light gets around to neighboring respective light receiving surfaces of the arrayed photodiodes. This reduces the relative intensity of light signals and deteriorates the S/N ratio.

The present invention is to solve the above-mentioned problems, and an object thereof is to provide a highly miniaturized biosensor and a sensor unit to be used in this biosensor, which can meet a demand for further miniaturization. With this invention, miniaturization is possible, and the number of production steps including those for assembling individual parts can be reduced. Accordingly, mass production will be possible, and cost reduction and high reliability will be achieved.

Means for Solving the Problems

In order to resolve the above-mentioned issues, a sensor unit of the present invention is to be included in a biosensor that measures values concerning liquid matter inside living tissue by irradiating light emitted from a light emitting unit toward the living tissue situated outside and receiving scattered light from the living tissue by a light receiving unit. The sensor unit is characterized by having a structure in which the light emitting unit and the light receiving unit are disposed on the same recess formed on a surface of a semiconductor substrate; a light shielding cover substrate having a light guiding section is disposed on an upper side of the semiconductor substrate; a light receiving surface of the light receiving unit is connected to one end of the light guiding section so as to conform to each other without any gap; light emitted from the light emitting unit is irradiated toward the living tissue situated outside; and scattered light from the living tissue passes through the light guiding section and is received by the light receiving unit.

By ensuring that the light receiving surface of the light receiving unit is connected to one end of the light guiding section such that they conform to each other without any gap, scattered light is prevented from getting around to the light receiving unit without providing a barrier separating the light emitting unit and the light receiving unit. This improves the S/N ratio while facilitating the miniaturization of the sensor unit. Furthermore, since the light emitting unit and the light receiving unit can be disposed on the same recess without any barriers provided between the two, steps for producing the sensor unit can be simplified.

A sensor unit of the present invention is characterized in that the light emitting unit and the light receiving unit are monolithically integrated on the semiconductor substrate. Here, the monolithic integration of the light emitting unit and the light receiving unit on the semiconductor substrate means that the light emitting unit and the light receiving unit are formed on a single semiconductor substrate.

As a result, a light emitting device and a light receiving element need not be assembled individually but can be integrally formed within the precision of photolithography. Processing accuracy during production is thus improved and production steps can be simplified.

A sensor unit of the present invention can also be included in a biosensor that measures values concerning liquid matter inside living tissue by irradiating light emitted from a light emitting unit toward the living tissue situated outside and receiving transmitted light from the living tissue by a light receiving unit. The sensor unit can have a structure in which the light emitting unit is disposed within a first recess formed on a surface of a semiconductor substrate; the light receiving unit is disposed within a second recess which is another recess formed on the surface of the semiconductor substrate; a light shielding cover substrate having a light guiding section is provided so as to cover the second recess; a light receiving surface of the light receiving unit is connected to one end of the light guiding section so as to conform to each other without any gap; light emitted from the light emitting unit is irradiated toward the living tissue situated outside; and light transmitted through the living tissue passes through the light guiding section and is received by the light receiving unit.

With sensors having this structure, the measurement of liquid matter such as blood inside a living body can easily be taken by inserting a finger or the like between the light emitting unit and the light receiving unit.

A sensor unit of the present invention, when the light receiving unit is formed with arrayed light receiving elements, is characterized in that the same number of the light guiding sections as the light receiving elements are provided on the cover substrate; and the light receiving surface of the light receiving element is connected to one end of each of the light guiding sections so as to conform to each other without any gap. Here, the arrayed light receiving elements mean a plurality of light receiving elements arranged on a single plane.

This structure prevents scattered light from getting around to individual light receiving surfaces of the arrayed light receiving elements, and further prevents light that results from the interference of coherent light and backscatters to the individual light receiving elements from entering the light receiving surfaces of the light receiving elements. Accordingly, noise is reduced, and the S/N ratio is improved.

In the above-mentioned structures, the first light guiding section and the second light guiding section can be formed with a pinhole or an optical waveguide, so that an improvement of the S/N ratio can be achieved.

In the present invention, it is preferable that the ratio of the length of the light guiding section to its opening be 2.5 or more.

If the ratio of the length of the light guiding section to its opening is less than 2.5, then the width of the opening becomes relatively too large to maintain the interference-preventing capability.

A biosensor of the present invention is characterized by including the above-mentioned sensor unit of the present invention, and an integrated circuit that includes a circuit driving a light emitting unit and a digital signal processor processing signals received from the sensor unit and calculating values concerning liquid matter inside a living body.

By utilizing the sensor unit of the present invention, a demand for further miniaturization can be met, and a biosensor with an excellent S/N ratio can be realized.

EFFECTS OF THE INVENTION

According to the present invention, a highly miniaturized biosensor and sensor unit can be realized. They are small in size, and the number of steps for assembling individual parts as well as the number of fabrication steps can be reduced to enable mass production, thereby achieving cost reduction as well as high reliability.

BRIEF DESCRIPTION OF THE DRAWINGS

FIG. 8 illustrates measured data concerning the S/N ratio of blood flowmeters.

DESCRIPTION OF REFERENCE NUMERALS AND SYMBOLS

| | |
|---|---|
| 11 | sensor chip |
| 12 | amplifier |
| 13 | driving/calculation device |
| 14 | output unit |
| 15 | A/D converter |
| 16 | LD driver |
| 17 | digital signal processor (DSP) |
| 18 | power supply unit |
| 19 | interface |
| 21 | light emitting unit |
| 22 | light receiving unit |
| 23, 23a, 23b | semiconductor substrate |
| 24 | recess |
| 24a | first recess |
| 24b | second recess |
| 25 | first light guiding section |
| 26 | second light guiding section |
| 27, 27a, 27b | light shielding cover substrate |
| 28 | light receiving element |
| 29, 29a, 29b | transparent substrate |
| 30 | living tissue |
| 31 | light receiving surface |
| 32 | pinhole |
| 33 | optical waveguide |
| 40 | barrier |
| 41 | light shielding film |
| 42 | transparent substrate |
| 50 | edge receiving photodiode |
| 51 | light shielding structure |
| 52 | pinhole |
| 60 | mirror |
| 61 | edge emitting semiconductor laser |
| 62 | collimating lens |
| 70 | micromirror |
| 71 | semiconductor laser photodiode beam splitter |
| 72 | through-hole electrode |
| 73 | cavity-structured silicon |
| 74 | seal glass with a lens |
| 75 | through-hole |

DETAILED DESCRIPTION OF THE INVENTION

Hereinbelow, a sensor unit and a biosensor of the present invention will be described in accordance with their embodiments. In the following paragraphs, a case of a blood flowmeter will be described as an example of a biosensor.

Figure 1:
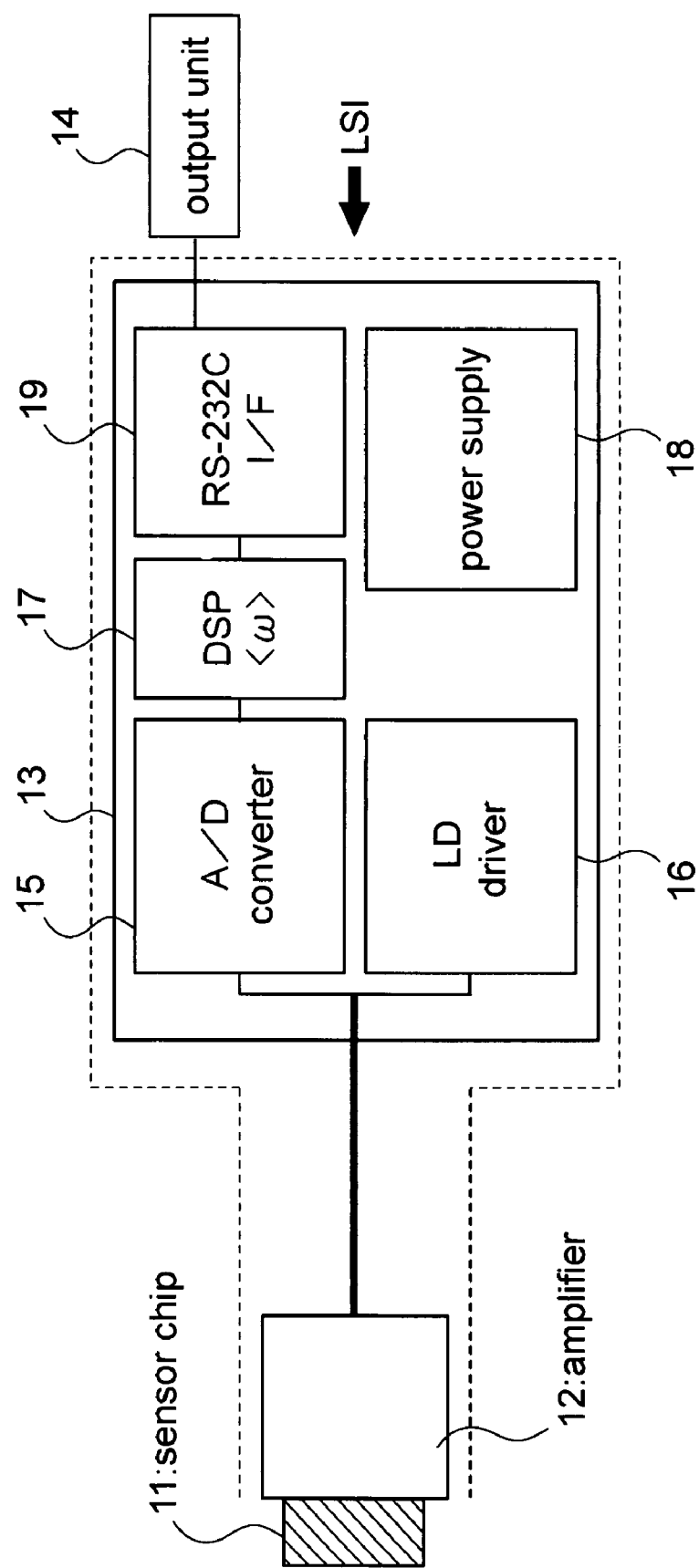
FIG. 1 illustrates the structure of a biosensor according to one embodiment of the present invention.

FIG. 1 illustrates a structure according to one embodiment of a biosensor of the present invention. As shown in FIG. 1, the biosensor of the present invention includes a sensor chip 11 that receives scattered light reflected at the living tissue when light is shone thereon, an amplifier 12 that amplifies received light, a driving/calculation device 13 that drives a light emitting device (LD) and calculates blood flow rates or the like by analyzing the scattered light, and an output unit 14 that displays obtained blood flow rates or the like. The sensor chip 11 is integrated and formed on a semiconductor substrate.

Furthermore, the driving/calculation device 13 includes an A/D converter 15, an LD driver 16, a digital signal processor (DSP) 17 that performs operations for obtaining blood flow rates from received signals, a power supply unit 18, and an interface 19. The driving/calculation device 13 is connected to the output unit 14 such as a small liquid crystal display. The whole of the driving/calculation device 13 can be structured as an LSI, integrating together with the sensor chip and the amplifier, so that it can be structured into a shape that allows simple installation onto a human body or the like.

Figure 2:
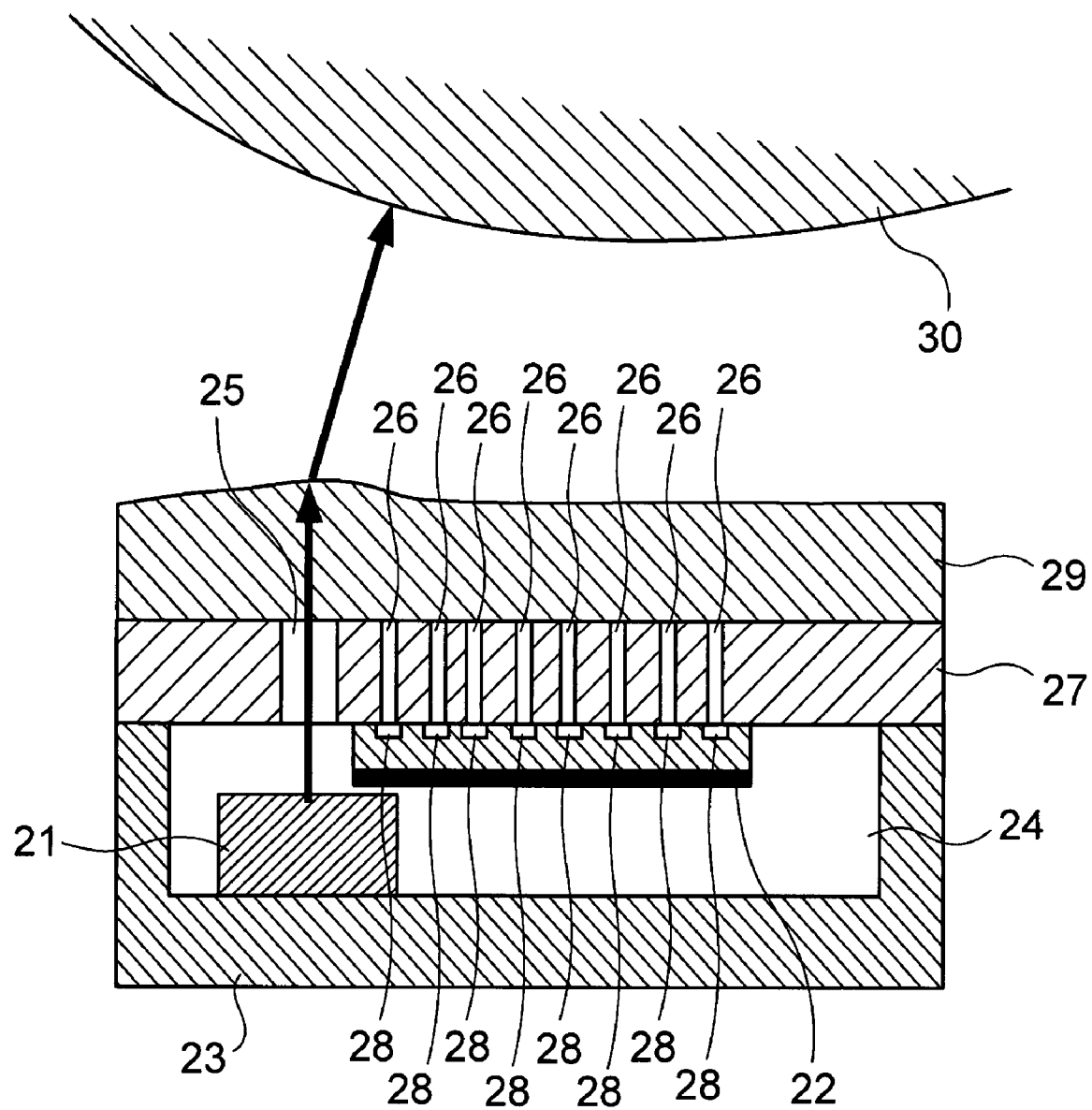
FIG. 2 illustrates one example of the structure of a sensor unit.
Figure 3:
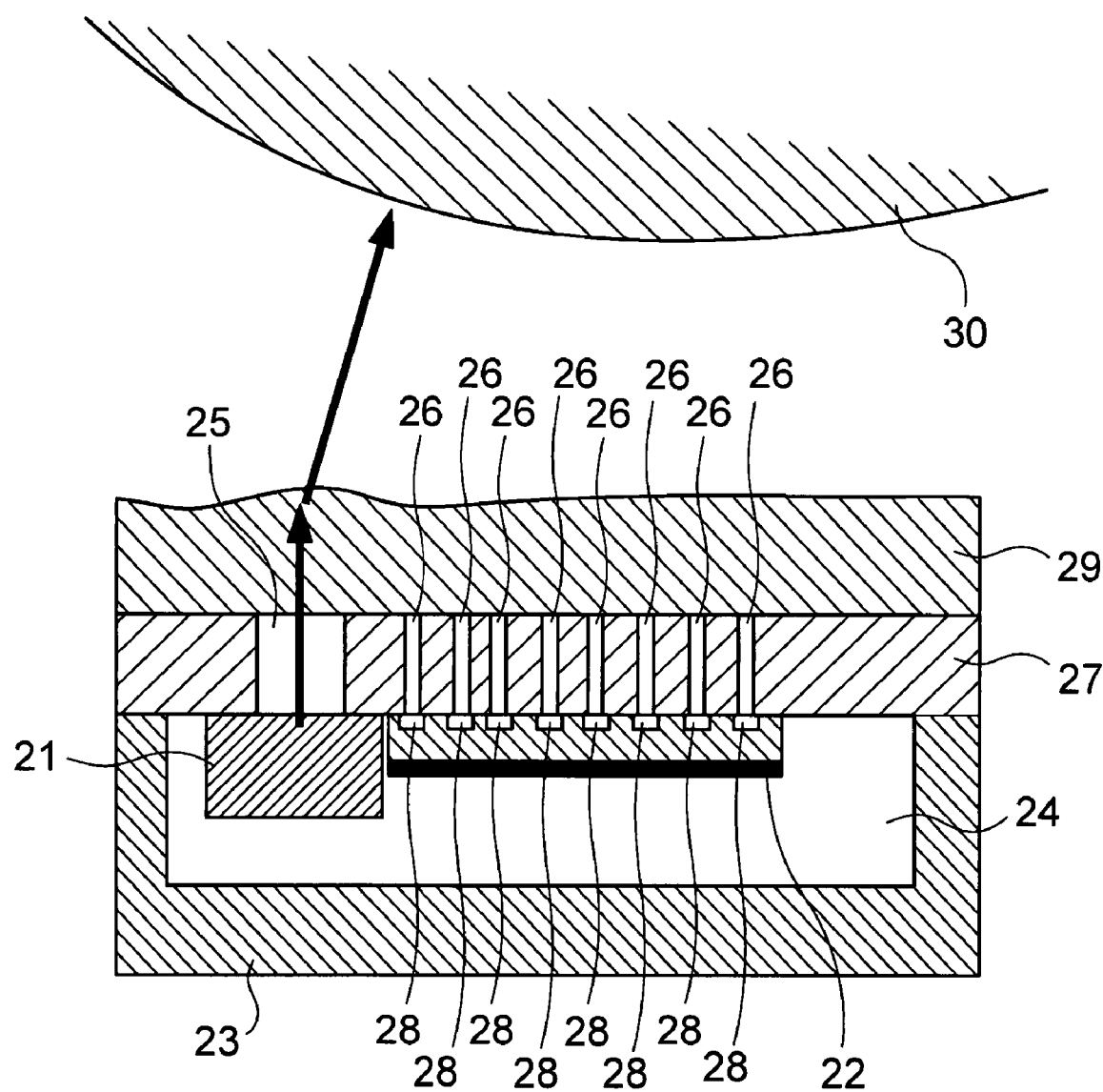
FIG. 3 illustrates another example of the structure of a sensor unit.

FIGS. 2 and 3 illustrate examples of the structure of the sensor unit. In these examples, the light receiving unit is formed with arrayed light receiving elements. In FIG. 2, the light emitting unit 21 and the light receiving unit 22 are disposed in a same recess 24 formed on a surface of a semiconductor substrate 23, and a light shielding cover substrate 27 that includes a first light guiding section 25 and second light guiding sections 26 are disposed on the upper side of the semiconductor substrate 23. Here, since the light receiving unit 22 is formed with arrayed light receiving elements 28, the same number of the second light guiding sections 26 as the light receiving elements 28 are provided to the light shielding cover substrate 27. A light receiving surface of the light receiving element 28 is connected to one end of corresponding one of the second light guiding sections 26 so as to conform to each other without any gap. Needless to say, when the light receiving unit 22 is formed with a single light receiving element 28, the number of the second light guiding section 26 to be provided to the light shielding cover substrate 27 is just one, and the light receiving surface of the light receiving unit 22 is connected to one end of the second light guiding section 26 so as to conform to each other without any gap. A transparent substrate 29 is provided on the upper side of the light shielding cover substrate 27. A semiconductor laser can be used as the light emitting unit 21, and a photodiode can be used as the light receiving unit 22. An example of the semiconductor laser is a DFB (Distributed Feedback) laser with the wavelength of 1.3 μm. By using such a DFB laser with the wavelength of 1.3 μm, light can reach deep into the subcutaneous tissue, and consistent waveforms can be detected.

In this structure, light emitted from the light emitting unit 21 passes through the first light guiding section 25 and is irradiated toward living tissue 30 situated outside, and scattered light from the living tissue 30 passes through the second light guiding sections 26 and is received by the light receiving unit 22.

In this example, although the light emitting unit 21 is provided on a surface of the semiconductor substrate 23, it can also be provided so that the light emitting surface of the light emitting unit 21 is connected to one end of the first light guiding section 25 so as to conform to each other without any gap as shown in FIG. 3.

In the description using FIGS. 2 and 3, although light from the light emitting unit 21 is irradiated toward the living tissue 30 through the first light guiding section 25, the first light guiding section 25 is not necessarily be required to guide light as such. Light from the light emitting unit 21 is only required to be irradiated toward the living tissue 30 by whatever the means available.

Figure 4A:
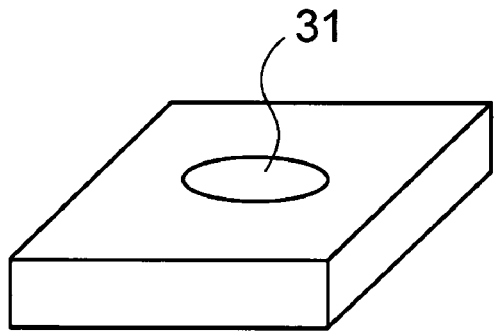
FIG. 4A illustrates a light receiving surface of a light receiving unit.
Figure 4B:
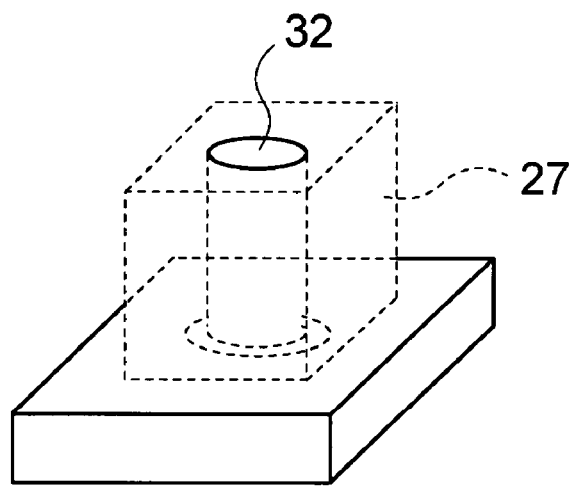
FIG. 4B illustrates a positional relationship between the light receiving surface of the light receiving unit and light guiding means.
Figure 4C:
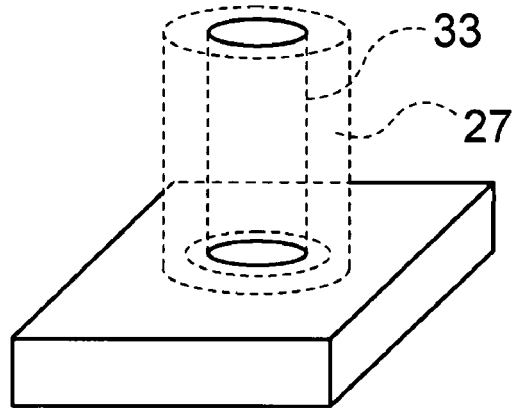
FIG. 4C illustrates a positional relationship between the light receiving surface of the light receiving unit and the light guiding means.

The present invention is particularly characterized in that, for a light receiving surface 31 of the light receiving unit shown in FIG. 4A, a pinhole 32 or an optical waveguide 33 is provided in the light shielding cover substrate 27 as the light guiding section as shown in FIGS. 4B and 4C, and this pinhole 32 or optical waveguide 33 is intimately connected to the light receiving surface 31 of the light receiving unit without any gap. In other words, the gap between an end of the light guiding section and the light receiving surface 31 is infinitesimally close to 0, and the light receiving surface 31 is situated inside an exterior wall of the light guiding section. Furthermore, this light guiding section is characterized in that the side of the light guiding section is shielded against light, and an opening of the light guiding section is small in comparison with its length.

Figure 5:
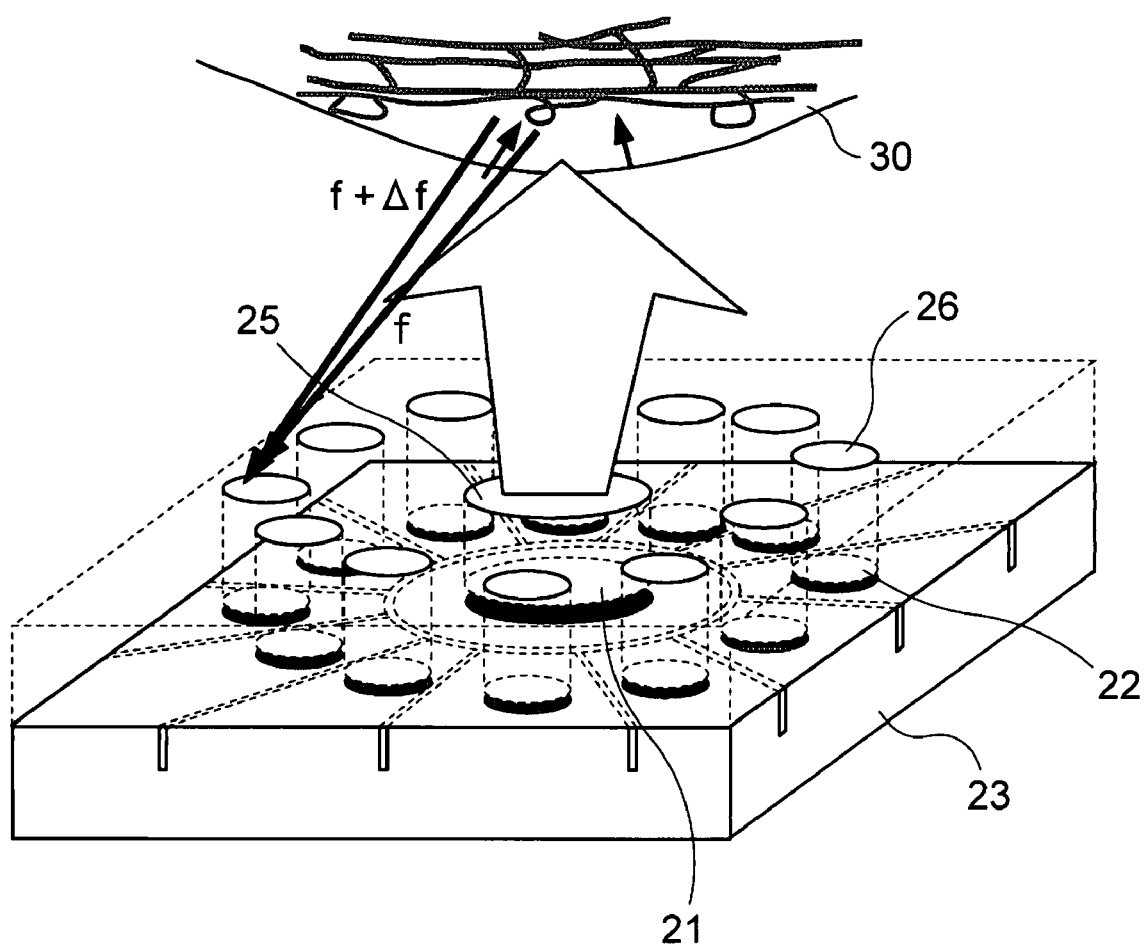
FIG. 5 illustrates one example of the light emitting unit and the light receiving units monolithically integrated on a semiconductor substrate.

FIG. 5 illustrates an example where the light emitting unit 21 and the light receiving unit 22 are monolithically integrated on the semiconductor substrate 23. In this example, the light emitting unit 21 is formed in a central area of the semiconductor substrate 23, and a pinhole acting as the first light guiding section 25 is provided on the light emitting unit 21 while making intimate contact therewith. Furthermore, a plurality of light receiving units 22 is formed so as to surround the light emitting unit 21, and pinholes serving as the second light guiding sections 26 are provided on the light receiving units 22 while making intimate contact therewith. Here again, optical waveguides can be used instead of pinholes. According to this structure, too, light emitted from the light emitting unit 21 is irradiated toward the living tissue 30 situated outside through the first light guiding section 25, and scattered light from the living tissue 30 passes through the second light guiding sections 26 and is received by the light receiving units 22.

Next, S/N ratios obtained with the blood flowmeters in which sensor units having the above-mentioned structures of the present invention are used will be described in comparison with conventional technology.

Figure 6A:
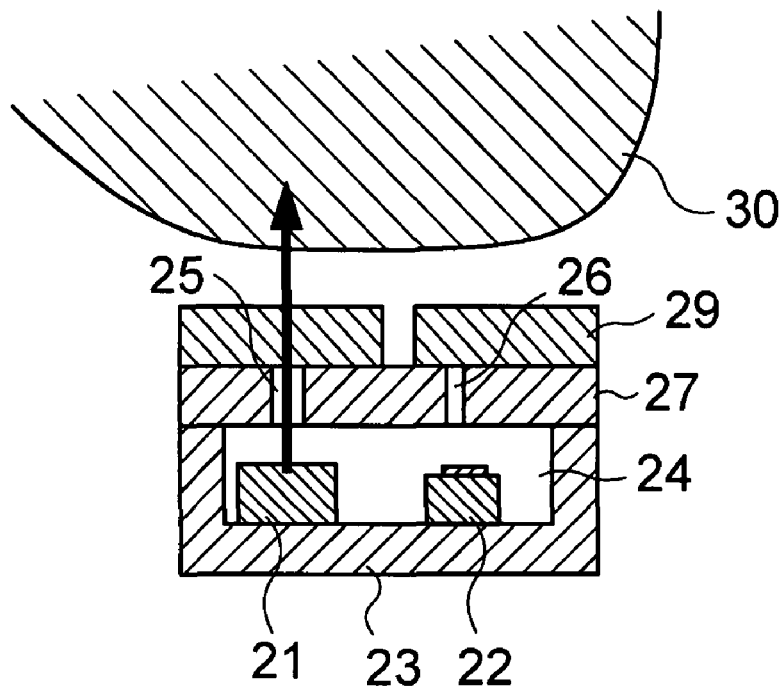
FIG. 6A illustrates one example of experiment when the light receiving unit is formed with a single light receiving element.
Figure 6B:
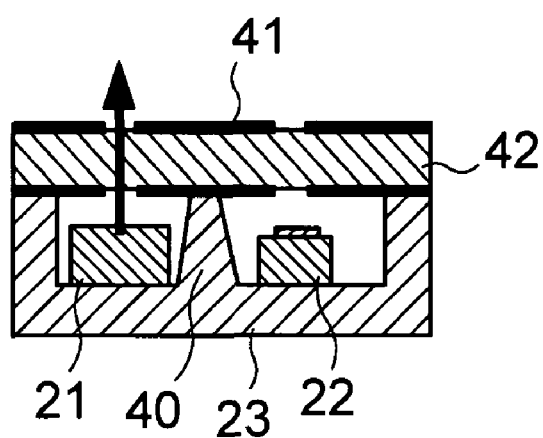
FIG. 6B illustrates one example of experiment when the light receiving unit is formed with a single light receiving element.
Figure 6C:
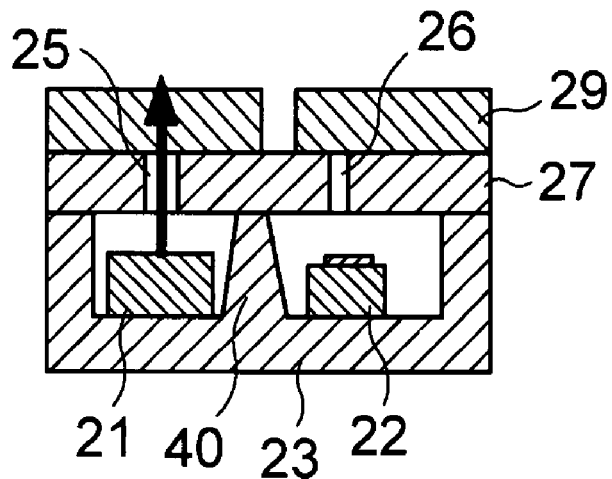
FIG. 6C illustrates one example of experiment when the light receiving unit is formed with a single light receiving element.
Figure 6D:
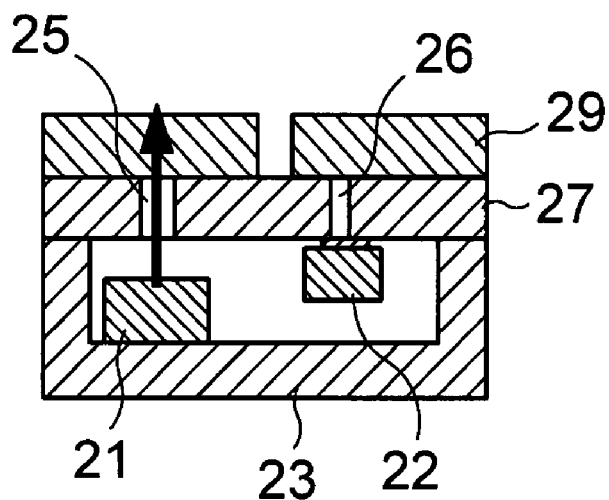
FIG. 6D illustrates one example of experiment when the light receiving unit is formed with a single light receiving element.

FIGS. 6A to 6D illustrate cases where the light receiving unit is formed with a single light receiving element. FIGS. 6A, 6B and 6C are for conventional technology, and FIG. 6D is for the structure of the present invention.

In FIG. 6A, the light emitting unit 21 and the light receiving unit 22 are disposed side by side on a surface of the semiconductor substrate 23, both being within the same recess 24 formed on a surface of the semiconductor substrate 23. A light shielding cover substrate 27 provided with the first light guiding section 25 and the second light guiding section 26 and a transparent substrate 29 are also disposed. There is a gap between the light receiving surface of the light receiving unit 22 and the second light guiding section 26.

In FIG. 6B, the light emitting unit 21 and the light receiving unit 22 are disposed side by side on a surface of the semiconductor substrate 23 with a barrier 40 separating the two, and a transparent substrate 42 is partially provided with a light shielding film 41. In FIG. 6C, the light emitting unit 21 and the light receiving unit 22 are disposed side by side on a surface of the semiconductor substrate 23 with the barrier 40 separating the two. The light shielding cover substrate 27 provided with the first light guiding section 25 and the second light guiding section 26 and the transparent substrate 29 are also disposed. There is a gap between the light receiving surface of the light receiving unit 22 and the second light guiding section 26.

In FIG. 6D, the light emitting unit 21 and the light receiving unit 22 are disposed within the same recess 24 formed on a surface of the semiconductor substrate 23. The light shielding cover substrate 27 provided with the first light guiding section 25 and the second light guiding section 26 and the transparent substrate 29 are also disposed. The light receiving surface of the light receiving unit 22 is intimately connected to the second light guiding section 26 so that there is not any gap between the two.

Figure 7A:
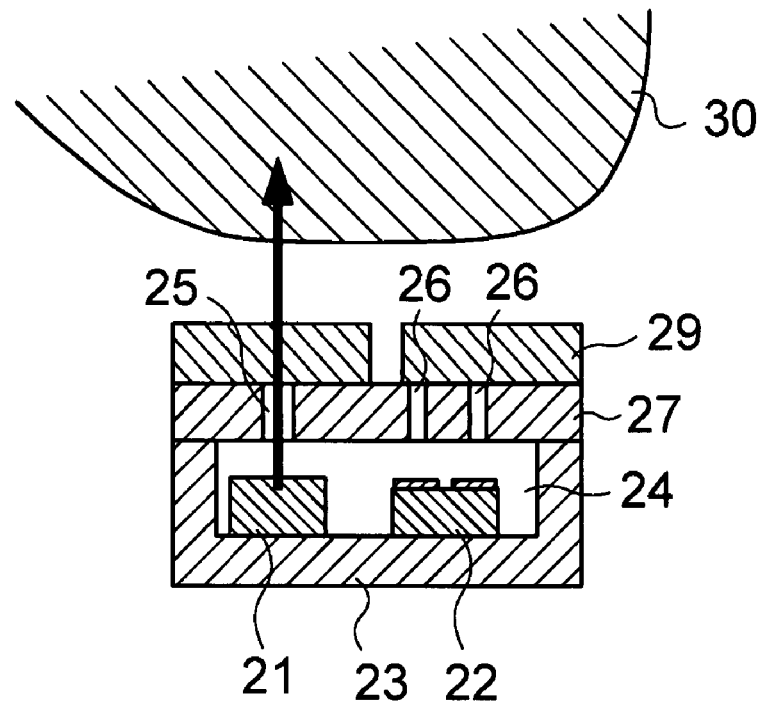
FIG. 7A illustrates one example of experiment when the light receiving unit is formed with arrayed light receiving elements.
Figure 7B:
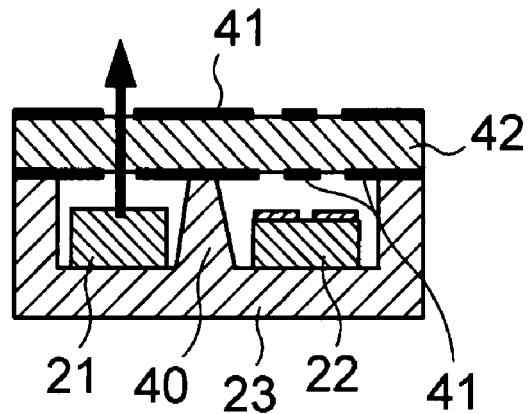
FIG. 7B illustrates one example of experiment when the light receiving unit is formed with arrayed light receiving elements.
Figure 7C:
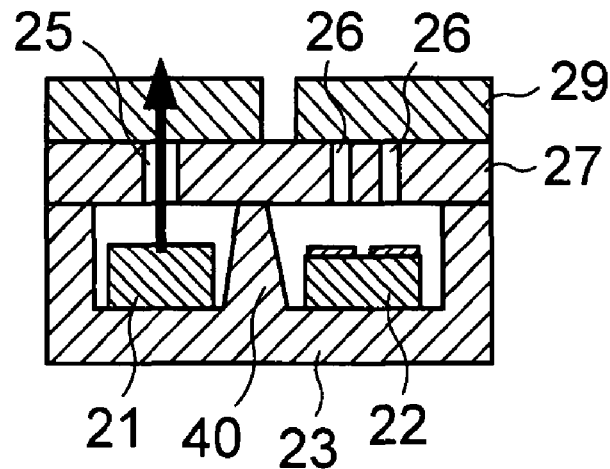
FIG. 7C illustrates one example of experiment when the light receiving unit is formed with arrayed light receiving elements.
Figure 7D:
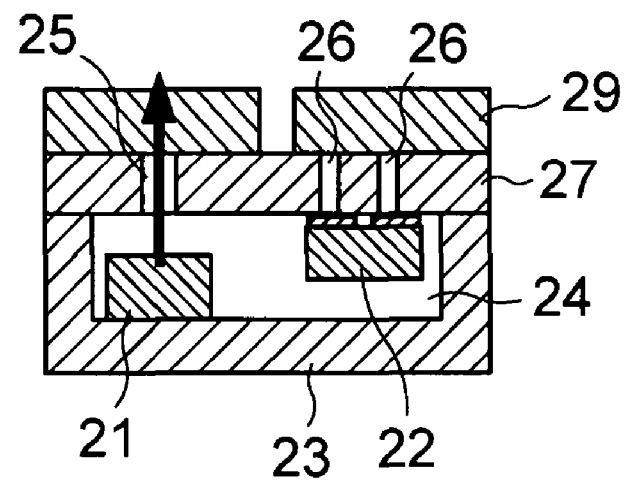
FIG. 7D illustrates one example of experiment when the light receiving unit is formed with arrayed light receiving elements.

FIGS. 7A to 7D illustrate cases where the light receiving unit is formed with arrayed light receiving elements. FIGS. 7A, 7B and 7C are for conventional technology, and FIG. 7D is for the structure of the present invention.

In FIG. 7A, the light emitting unit 21 and the light receiving unit 22 are disposed side by side on a surface of the semiconductor substrate 23, both being within the same recess 24 formed on a surface of the semiconductor substrate 23. The light shielding cover substrate 27 provided with the first light guiding section 25 and the second light guiding sections 26 and the transparent substrate 29 are also disposed. There is a gap between the light receiving surface of each light receiving element of the light receiving unit 22 and the corresponding one of the second light guiding sections 26.

In FIG. 7B, the light emitting unit 21 and the light receiving unit 22 are disposed side by side on a surface of the semiconductor substrate 23 with the barrier 40 separating the two, and the transparent substrate 42 is partially provided with the light shielding film 41. In FIG. 7C, the light emitting unit 21 and the light receiving unit 22 are disposed side by side on a surface of the semiconductor substrate 23 with the barrier 40 separating the two. The light shielding cover substrate 27 provided with the first light guiding section 25 and the second light guiding sections 26 and the transparent substrate 29 are also disposed. There is a gap between the light receiving surface of each light receiving element of the light receiving unit 22 and the corresponding one of the second light guiding sections 26.

In FIG. 7D, the light emitting unit 21 and the light receiving unit 22 are disposed within the same recess 24 formed on a surface of the semiconductor substrate 23. The light shielding cover substrate 27 provided with the first light guiding section 25 and the second light guiding sections 26 and the transparent substrate 29 are also disposed. The light receiving surface of each light receiving element of the light receiving unit 22 is intimately connected to the corresponding one of the second light guiding sections 26 so that there is not any gap between the two.

FIG. 8 shows measured data concerning the S/N ratios of blood flowmeters for the cases where the structure of the sensor unit is as illustrated in each of FIGS. 6A to 6D and FIGS. 7A to 7D. As can be seen from FIG. 8, exceptionally excellent S/N ratios were obtained in experiments D and H where the structure of the present invention was employed. In particular, the S/N ratio was significantly improved in the case where the light receiving unit is formed with arrayed light receiving elements.

Figure 9:
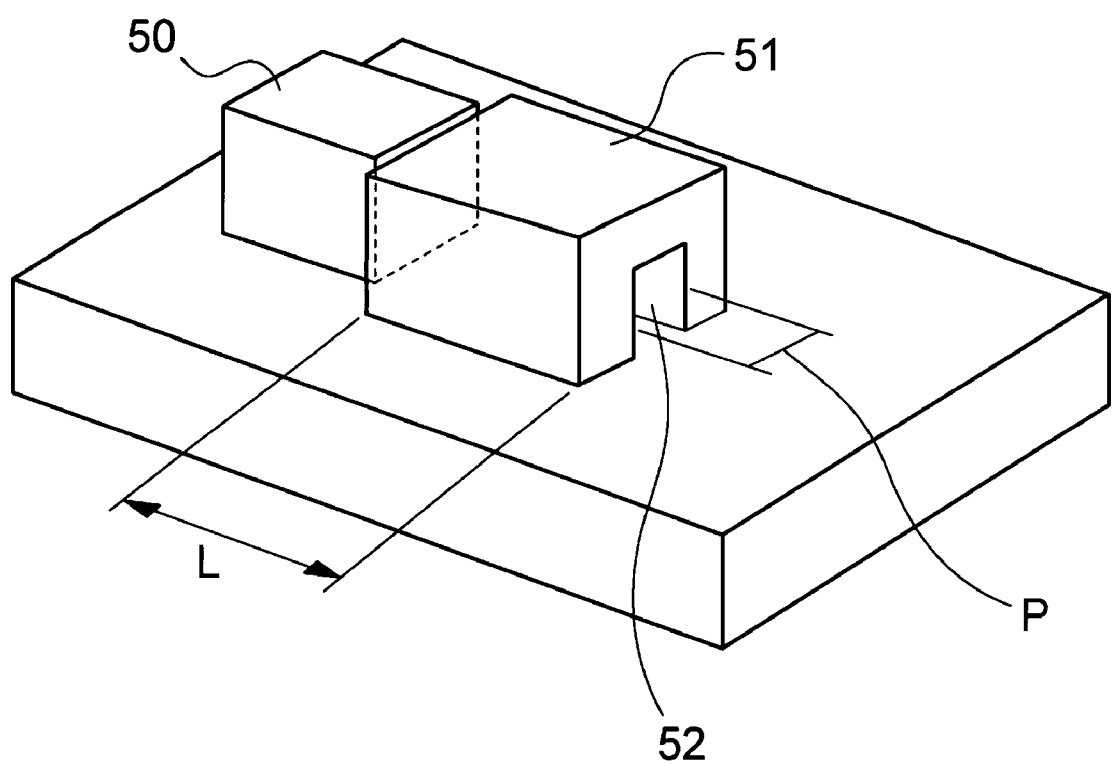
FIG. 9 explains about an optimum range of shapes of a pinhole or an optical waveguide as light guiding means.

An optimum range of shapes of a pinhole or an optical waveguide as light guiding means will be described in accordance with FIG. 9. In FIG. 9, an edge receiving photodiode 50 is used as the light receiving unit, and a light shielding structure 51 that has a pinhole 52 is disposed so as to make intimate contact with the light receiving surface of the edge receiving photodiode 50. Then, a ratio of the length L of the pinhole 52 to the width P of the opening, namely, L/P (hereinafter, referred to as "aspect ratio"), was changed, and the S/N ratio was measured. The results were shown in Table 1.

TABLE 1

| | Dimensions of light shielding structure | | Relative S/N ratio (S/N ratio with respect to edge receiving PD without light shielding structure) |
|---|---|---|---|
| | P | L | |
| Surface receiving PD (light receiving unit approximately 200 microns × 200 microns) | No light shielding structure | | No signals detected |
| Edge receiving PD | No light shielding structure | | Signals detected, 1 |
| | 57 microns | 500 microns | 9 |
| | 200 microns | | 2.5 |
| | 340 microns | | 1.5 |

From these results, it is preferable that the aspect ratio be 2.5 or more. If the aspect ratio is less than 2.5, then the width P of the opening will become relatively too large, and the interference-preventing capability will be deteriorated. Under the conditions of this experiment, it has been confirmed that excellent S/N ratios can be obtained when L/P is approximately 8.

As described so far, in a sensor unit of the present invention, light emitted from the light emitting unit 21 is irradiated on living tissue situated outside as illustrated in FIGS. 2, 3 and 5. When this sensor chip is brought close to living tissue such as a skin, light scattering takes place, and scattered light enters again the light receiving unit 22. This scattered light includes an interference component resulting from the scattered light from the living tissue at rest and the scattered light from red corpuscles moving through a capillary (Doppler-shifted light). Hence, by conducting frequency analysis on these signals, velocity of blood flow can be determined. Furthermore, since intensity of scattered light corresponds to the volume of moving blood, blood flow rate can be obtained as a product of the velocity of blood flow and the volume of blood. Furthermore, since waveforms of the scattered signals include modulated components due to a pulse, a pulse rate can also be determined.

Figure 10:
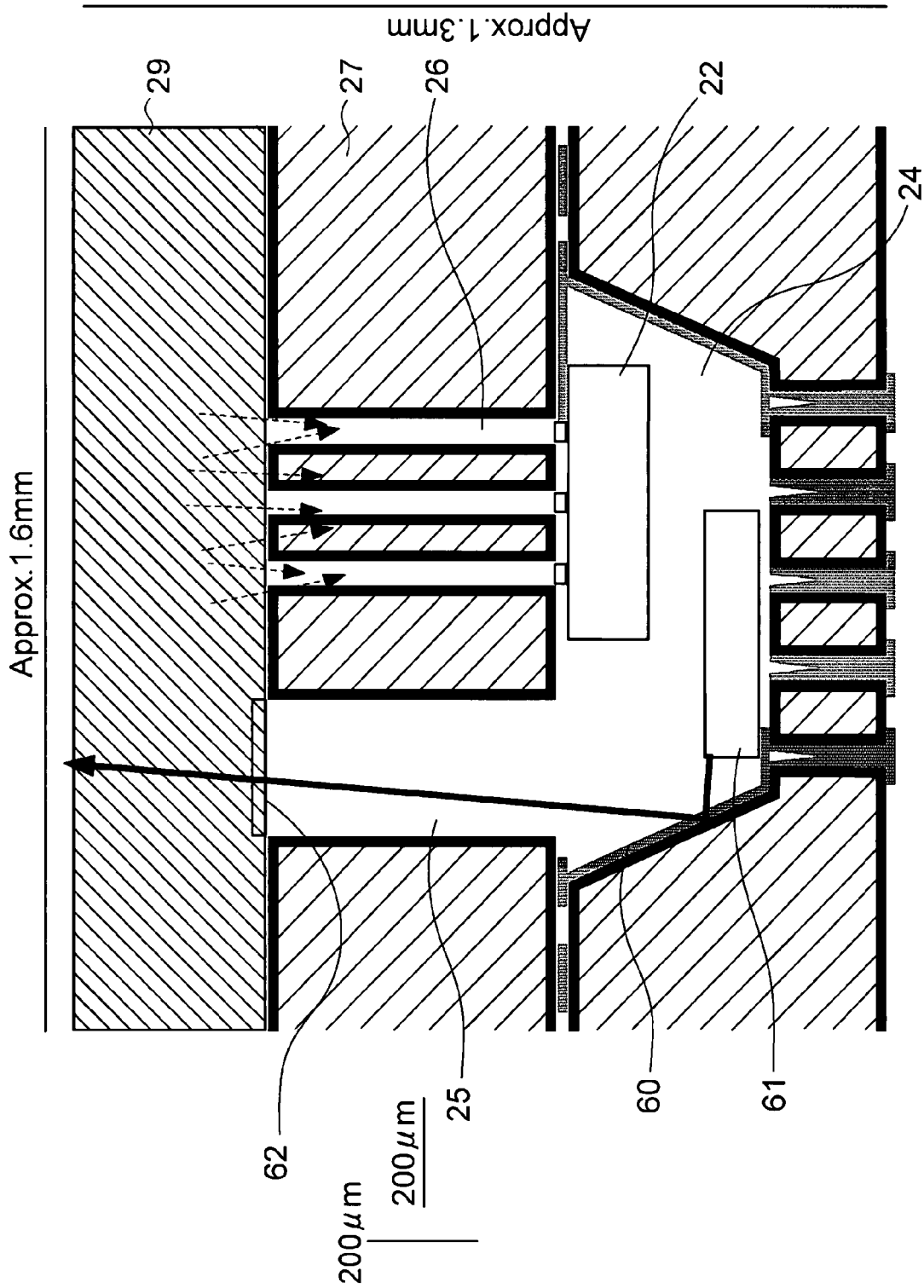
FIG. 10 illustrates a case where an edge emitting semiconductor laser is used as the light emitting unit.

The structure of the light emitting unit is not limited to those illustrated in FIGS. 2 and 3. Structures illustrated in FIGS. 10 and 11 can also be employed. In FIG. 10 that illustrates the case where an edge emitting semiconductor laser is used, a mirror 60 is formed on part of the recess 24, and light emitted from an end of the edge emitting semiconductor laser 61 is reflected upward by the mirror 60 and irradiated toward the living tissue situated outside through the first light guiding section 25 via a collimating lens 62. Scattered light from the living tissue is received by the light receiving unit 22 through the second light guiding section 26 provided in the light shielding cover substrate 27.

Figure 11:
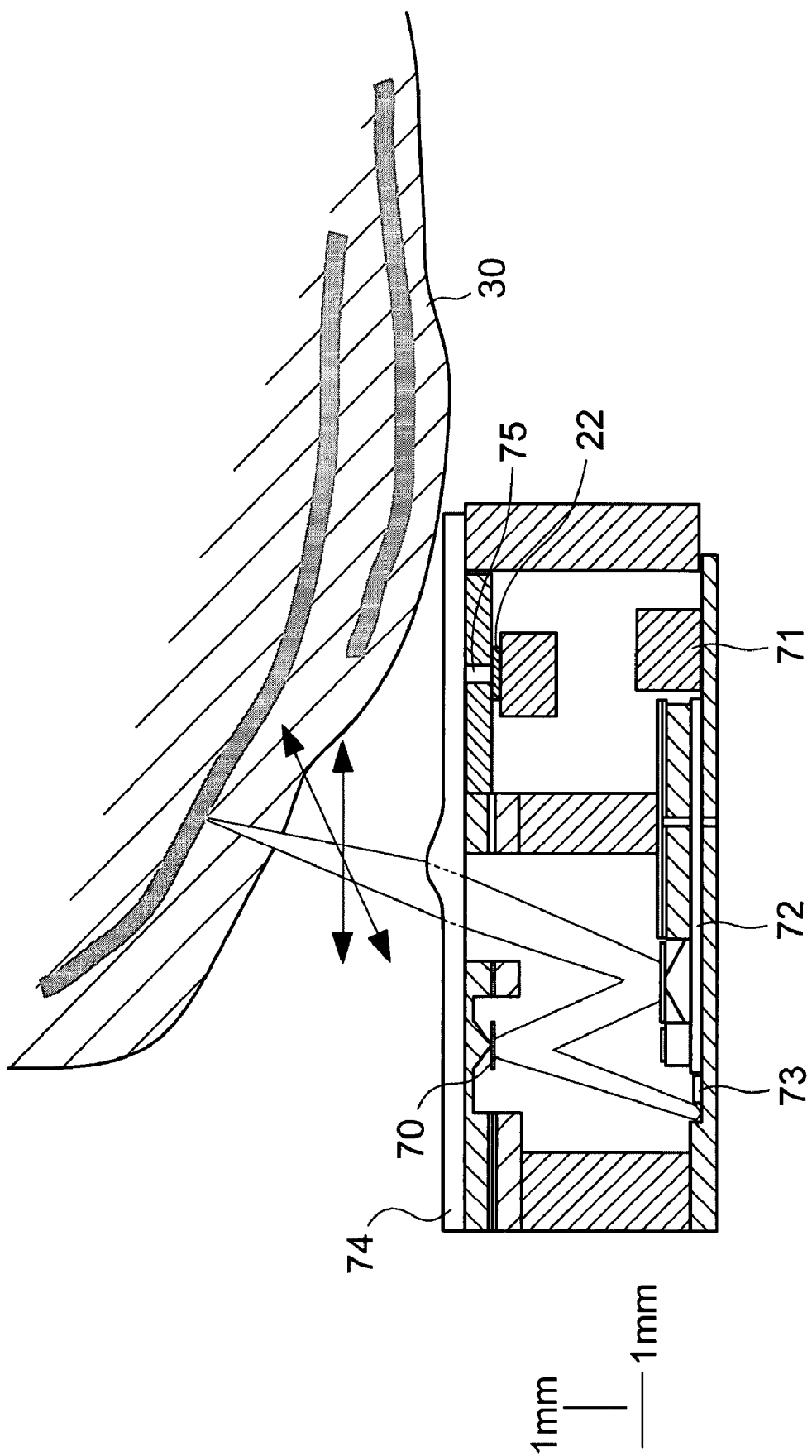
FIG. 11 illustrates a case where a micromirror is used for emitting light toward living tissue.

FIG. 11 illustrates a structure where a micromirror is used when discharging light toward living tissue 30. In the figure, by scanning with a micromirror 70 and utilizing a beam of a microscanning microscope condensed by a lens or the like, not only an observation of the living tissue but also blood flow rates or flow of liquid matter inside living tissue at the observation point can be measured at the same time. Also present in FIG. 11 are a semiconductor laser photodiode beam splitter 71, a through-hole electrode 72, a cavity-structured silicon 73, a seal glass 74 with a lens, a through-hole 75, and the light receiving unit 22.

Figure 12:
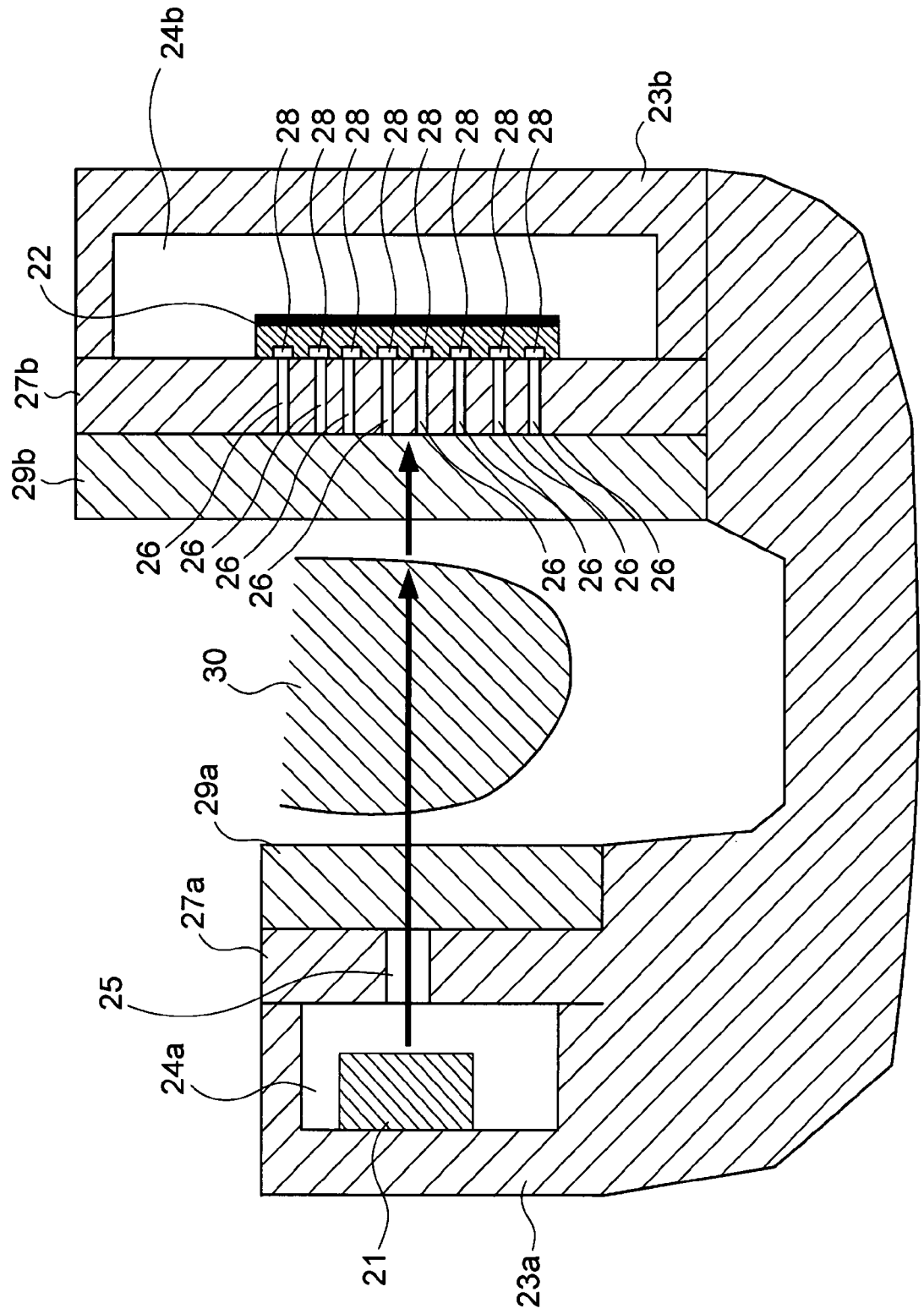
FIG. 12 illustrates one example of the structure of a sensor unit according to another embodiment.
Figure 13:
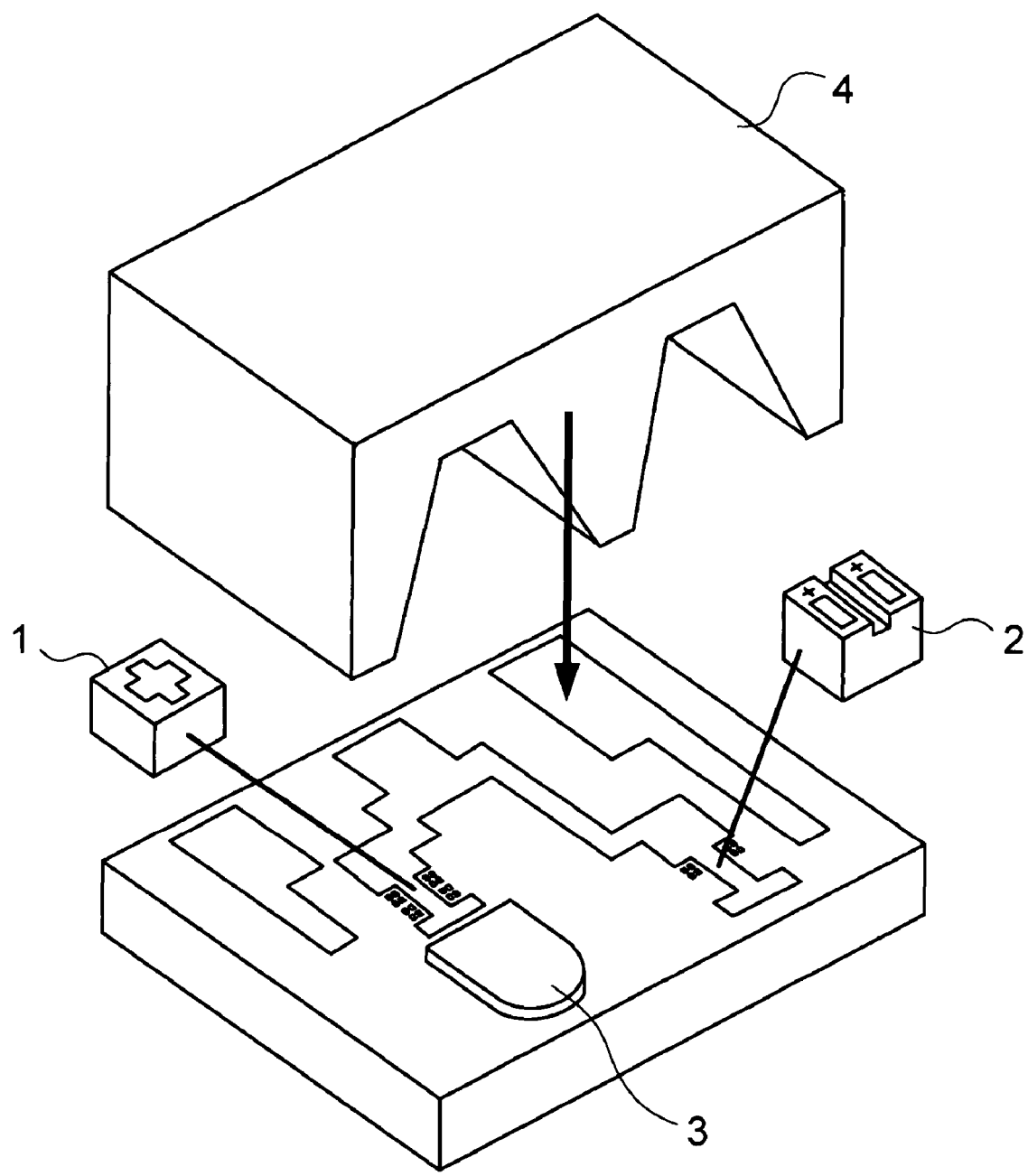
FIG. 13 illustrates a sensor chip of a conventional blood flowmeter.

FIG. 12 illustrates one example of the structure of a sensor unit according to another embodiment. In this example, the light receiving unit is formed with arrayed light receiving elements. In FIG. 12, the light emitting unit 21 is disposed within a first recess 24a formed on a surface of a semiconductor substrate 23a, and the light receiving unit 22 is disposed within another recess, namely, a second recess 24b, formed on a surface of a semiconductor substrate 23b.

A light shielding cover substrate 27a having the first light guiding section 25 is disposed so as to cover the first recess 24a, and a transparent substrate 29a is provided on an upper side of the light shielding cover substrate 27a. Furthermore, another light shielding cover substrate 27b having the second light guiding section 26 is disposed so as to cover the second recess 24b, and a transparent substrate 29b is provided on an upper side of the light shielding cover substrate 27b.

Here, since the light receiving unit 22 is formed with the arrayed light receiving elements 28, the same number of second light guiding sections 26 as the light receiving elements 28 are provided in the light shielding cover substrate 27b, and each light receiving surface of the light receiving elements 28 is connected to one end of corresponding one of the second light guiding sections 26 so as to conform to each other without any gap. Needless to say, when the light receiving unit 22 is formed with a single light receiving element 28, the number of the second light guiding section 26 to be provided to the light shielding cover substrate 27b is just one, and the light receiving surface of the light receiving unit 22 is connected to one end of the second light guiding section 26 so as to conform to each other without any gap. A semiconductor laser can be used as the light emitting unit 21, and photodiodes can be used as the light receiving unit 22. An example of the semiconductor laser is a DFB laser with the wavelength of 1.3 μm. By using such a DFB laser with the wavelength of 1.3 μm, light can reach deep into the subcutaneous tissue, and consistent waveforms can be detected.

In the description using FIG. 12, although light from the light emitting unit 21 is irradiated toward the living tissue 30 through the first light guiding section 25, the first light guiding section 25 is not necessarily be required to guide light as such. Light from the light emitting unit 21 is only required to be irradiated toward the living tissue 30 by whatever the means available.

With this sensor unit, inserting living tissue 30 such as a finger between the light emitting side and the light receiving side allows the detection at the light receiving unit 22 of light that is emitted from the light emitting unit 21 and transmitted through the living tissue 30. Hence, the measurement of blood flow can be taken by a simple method.

Although, in any of the above-mentioned embodiments, the cases where a sensor unit of the present invention is used in a blood flowmeter, this sensor unit is not limited to use in blood flowmeters but is applicable to other subjects that can be measured based on the principles described above. For example, the sensor unit is capable of detecting the flow of liquid matter inside a living body, such as the flow of gel matter inside cartilage, and can be used widely as biosensors.

Industrial Applicability

The present invention is configured such that the bonding of light shielding cover substrates with optical elements or light guiding sections and seal substrates or the like can be conducted on a wafer level, and such a wafer can be diced in the last production step to yield individual sensors. Therefore, miniaturization is possible, and the number of production steps including those for assembling individual parts can be reduced, thereby contributing to the progress of mass production. The present invention can provide a highly miniaturized biosensor and a sensor unit that is capable of reducing costs and ensuring high reliability.

The invention claimed is:

1. A sensor unit which is to be included in a biosensor that measures values concerning liquid matter inside living tissue by irradiating light toward the living tissue situated outside and receiving scattered light from the living tissue, the sensor unit comprising:
   a light emitting unit and a light receiving unit disposed in a same recess formed on a surface of a semiconductor substrate, the light receiving unit having one or more light receiving elements; and
   a light shielding cover substrate having one or more light guiding sections disposed on an upper side of the semiconductor substrate, the one or more light receiving elements and the one or more light guiding sections being provided in equal numbers,
   wherein a light receiving surface of each of the one or more light receiving elements is connected to one end of a respective one of the one or more light guiding sections so as to conform to each other without any gap therebetween,
   wherein light emitted from the light emitting unit is irradiated toward the living tissue situated outside, and scattered light from the living tissue passes through the one or more light guiding sections and is received by the one or more light receiving elements,
   wherein the one or more light guiding sections are each formed with a pinhole, and
   wherein a ratio of the length of the one or more light guiding sections to an opening thereof is 2.5 or more.

2. A sensor unit according to claim 1, wherein the light emitting unit and the light receiving unit are monolithically integrated on the semiconductor substrate.

3. A biosensor comprising:
   the sensor unit according to claim 1; and
   an integrated circuit including a circuit for driving the light emitting unit, and a digital signal processor for processing signals received from the sensor unit and calculating values concerning liquid matter inside a living body.

4. A biosensor comprising:
   the sensor unit according to claim 2; and
   an integrated circuit including a circuit for driving the light emitting unit, and a digital signal processor for processing signals received from the sensor unit and calculating values concerning liquid matter inside a living body.

* * * * *